United States Patent
Fairneny et al.

(10) Patent No.: US 9,282,956 B2
(45) Date of Patent: Mar. 15, 2016

(54) DEVICES AND METHODS FOR MANIPULATING BODILY TISSUES

(75) Inventors: Ty Fairneny, Hopkinton, MA (US); Dennis Miller, Whitefish Bay, WI (US); Michael F. Weiser, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 206 days.

(21) Appl. No.: 13/610,285

(22) Filed: Sep. 11, 2012

(65) Prior Publication Data

US 2013/0072749 A1     Mar. 21, 2013

Related U.S. Application Data

(60) Provisional application No. 61/535,095, filed on Sep. 15, 2011.

(51) Int. Cl.
| | |
|---|---|
| *A61F 2/00* | (2006.01) |
| *A61F 13/00* | (2006.01) |
| *A61B 17/02* | (2006.01) |
| *A61B 17/42* | (2006.01) |

(Continued)

(52) U.S. Cl.
CPC .............. *A61B 17/02* (2013.01); *A61B 17/0218* (2013.01); *A61B 17/4241* (2013.01); *A61B 17/0469* (2013.01); *A61B 19/5202* (2013.01); *A61B 2017/2927* (2013.01); *A61B 2019/4889* (2013.01)

(58) Field of Classification Search
CPC .... A61B 17/42; A61B 17/02; A61B 17/0218; A61B 2019/4889; A61B 17/4241; A61B 19/5202; A61B 2017/2927; A61B 17/0469
USPC .................. 600/37, 29, 20; 128/897–899
See application file for complete search history.

(56) References Cited

U.S. PATENT DOCUMENTS

| | | | |
|---|---|---|---|
| 1,615,728 A | * | 1/1927 | Smith ..................... A61D 9/02 |
| | | | 128/834 |
| 4,048,987 A | * | 9/1977 | Hurson ...................... 600/206 |

(Continued)

FOREIGN PATENT DOCUMENTS

| | | |
|---|---|---|
| DE | 202004015215 U1 | 12/2004 |
| FR | 2817731 A1 | 6/2002 |

(Continued)

OTHER PUBLICATIONS

International Search Report and Written Opinion received for PCT Patent Application No. PCT/US2012/054844, mailed on Oct. 17, 2012, 13 pages.

(Continued)

*Primary Examiner* — Navin Natnithithadha
*Assistant Examiner* — Sunita Reddy
(74) *Attorney, Agent, or Firm* — Brake Hughes Bellermann LLP

(57) ABSTRACT

A medical device and a method for manipulating bodily tissues are described. The medical device includes an elongated portion having a proximal end portion and a distal end portion. The elongated portion has a defined width referred to as first width. The medical device further includes a head portion extending from the distal end portion of the elongated portion. The head portion includes a first flat surface on a first side and a second flat surface on a second side opposite the first side. The head portion has a defined width referred to as second width. The second width is greater than the first width.

18 Claims, 15 Drawing Sheets

(51) Int. Cl.
*A61B 17/04* (2006.01)
*A61B 19/00* (2006.01)
*A61B 17/29* (2006.01)

(56) References Cited

U.S. PATENT DOCUMENTS

| | | | | |
|---|---|---|---|---|
| 4,226,228 | A | * | 10/1980 | Shin et al. .................... 600/206 |
| 4,241,912 | A | * | 12/1980 | Mercer ................. A63B 23/20 482/91 |
| 4,747,393 | A | | 5/1988 | Medwid |
| 4,784,150 | A | * | 11/1988 | Voorhies et al. ............. 600/473 |
| 4,881,526 | A | * | 11/1989 | Johnson ................ A61H 19/44 601/15 |
| 5,209,754 | A | | 5/1993 | Ahluwalia |
| 5,217,463 | A | | 6/1993 | Mikhail |
| 5,518,503 | A | | 5/1996 | Rooney et al. |
| 5,803,902 | A | * | 9/1998 | Sienkiewicz et al. ......... 600/203 |
| 6,165,108 | A | * | 12/2000 | Ralston ................. A63B 23/20 482/105 |
| 6,394,939 | B1 | * | 5/2002 | Stein ...................... A63B 23/20 482/148 |
| 7,001,317 | B2 | * | 2/2006 | Marcotte ................ A63B 23/20 128/833 |
| 2002/0000233 | A1 | * | 1/2002 | Jude ...................... A63B 23/20 128/897 |
| 2002/0116025 | A1 | | 8/2002 | Haab |
| 2004/0153065 | A1 | * | 8/2004 | Lim ................................ 606/53 |
| 2005/0277948 | A1 | | 12/2005 | Cedars et al. |
| 2006/0100475 | A1 | * | 5/2006 | White et al. ...................... 600/3 |
| 2007/0060795 | A1 | * | 3/2007 | Vayser et al. .................. 600/245 |
| 2007/0161849 | A1 | | 7/2007 | Goldberg |
| 2008/0081952 | A1 | | 4/2008 | Josephberg |
| 2008/0221384 | A1 | * | 9/2008 | Chi Sing et al. .................. 600/7 |
| 2009/0171143 | A1 | | 7/2009 | Chu et al. |
| 2009/0209973 | A1 | | 8/2009 | East |
| 2010/0137692 | A1 | | 6/2010 | Lindsay et al. |
| 2010/0286482 | A1 | * | 11/2010 | Rosenblatt .................... 600/202 |
| 2010/0305394 | A1 | * | 12/2010 | Rosenblatt ...................... 600/30 |
| 2013/0005543 | A1 | * | 1/2013 | Armitage ............... A63B 23/20 482/131 |
| 2013/0197537 | A1 | | 8/2013 | Fairneny et al. |

FOREIGN PATENT DOCUMENTS

| | | |
|---|---|---|
| GB | 1604168 A | 12/1981 |
| WO | 2009/076616 A2 | 6/2009 |
| WO | 2013/040022 A1 | 3/2013 |
| WO | 2014/143626 A1 | 9/2014 |

OTHER PUBLICATIONS

International Preliminary Report on Patentability received for PCT Patent Application No. PCT/US2012/054844, mailed on Mar. 27, 2014, 9 pages.

International Search Report and Written Opinion received for PCT Patent Application No. PCT/US2014/024814, mailed on May 9, 2014, 16 pages.

Puntambekar, et al., "A Novel Technique of Uterine Manipulation in Laparoscopic Pelvic Oncosurgical Procedures: 'The Uterine Hitch Technique'", Research Article, vol. 2010, Article Id 836027, Novembery 26, 2009, pp. 1-5.

Non-Final Office Action for U.S. Appl. No. 13/801,897, filed Mar. 27, 2015, 21 pages.

* cited by examiner

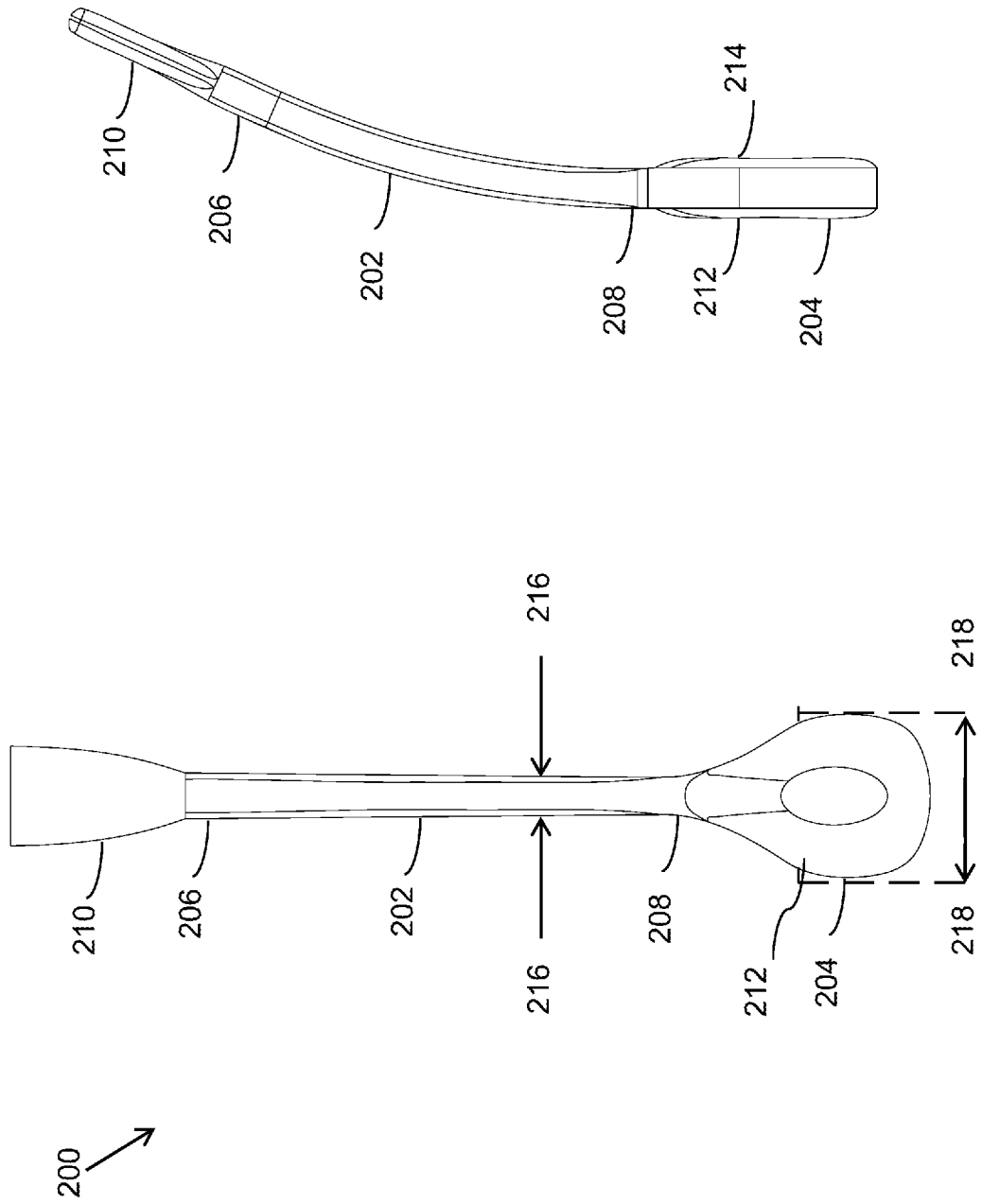

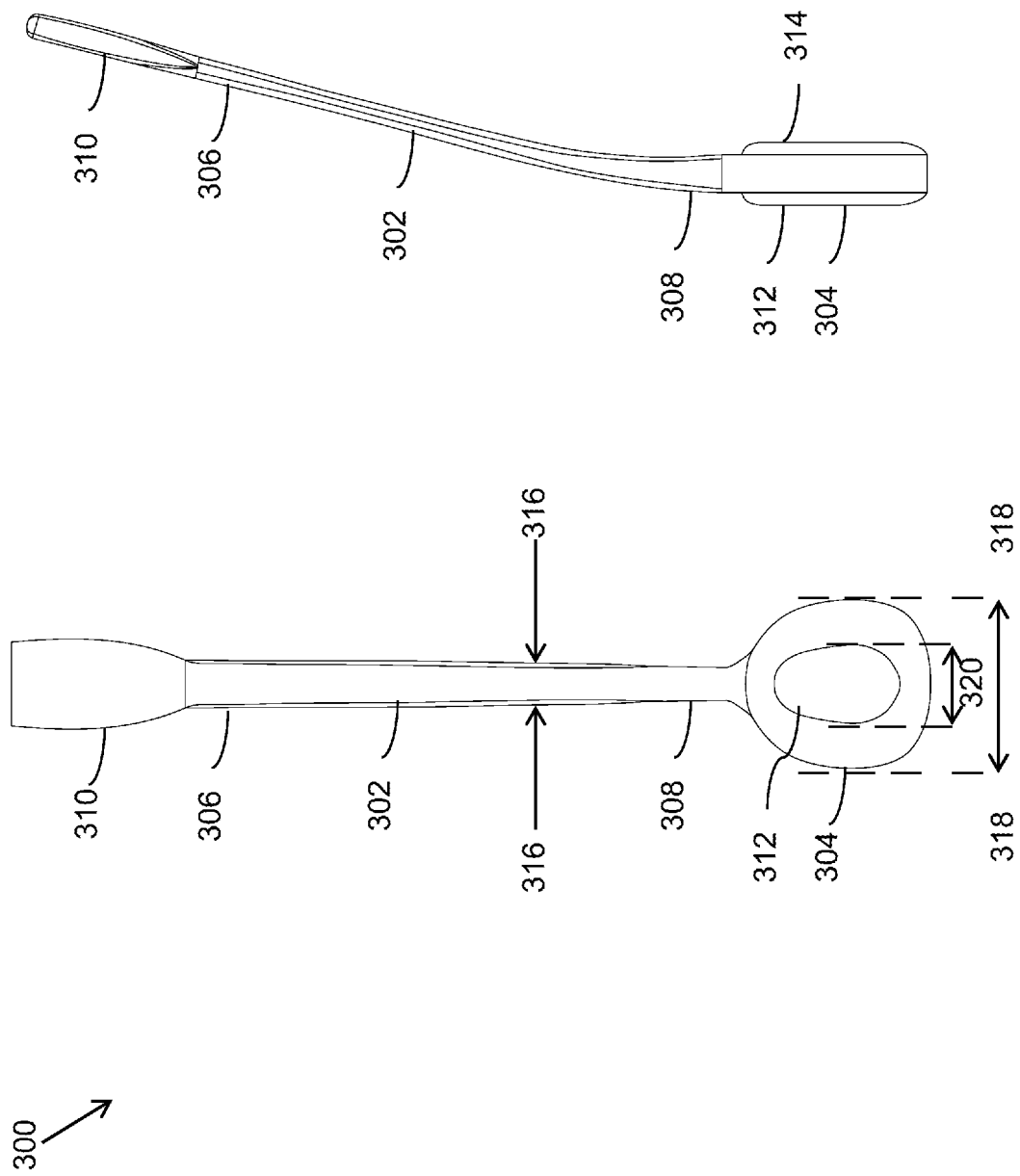

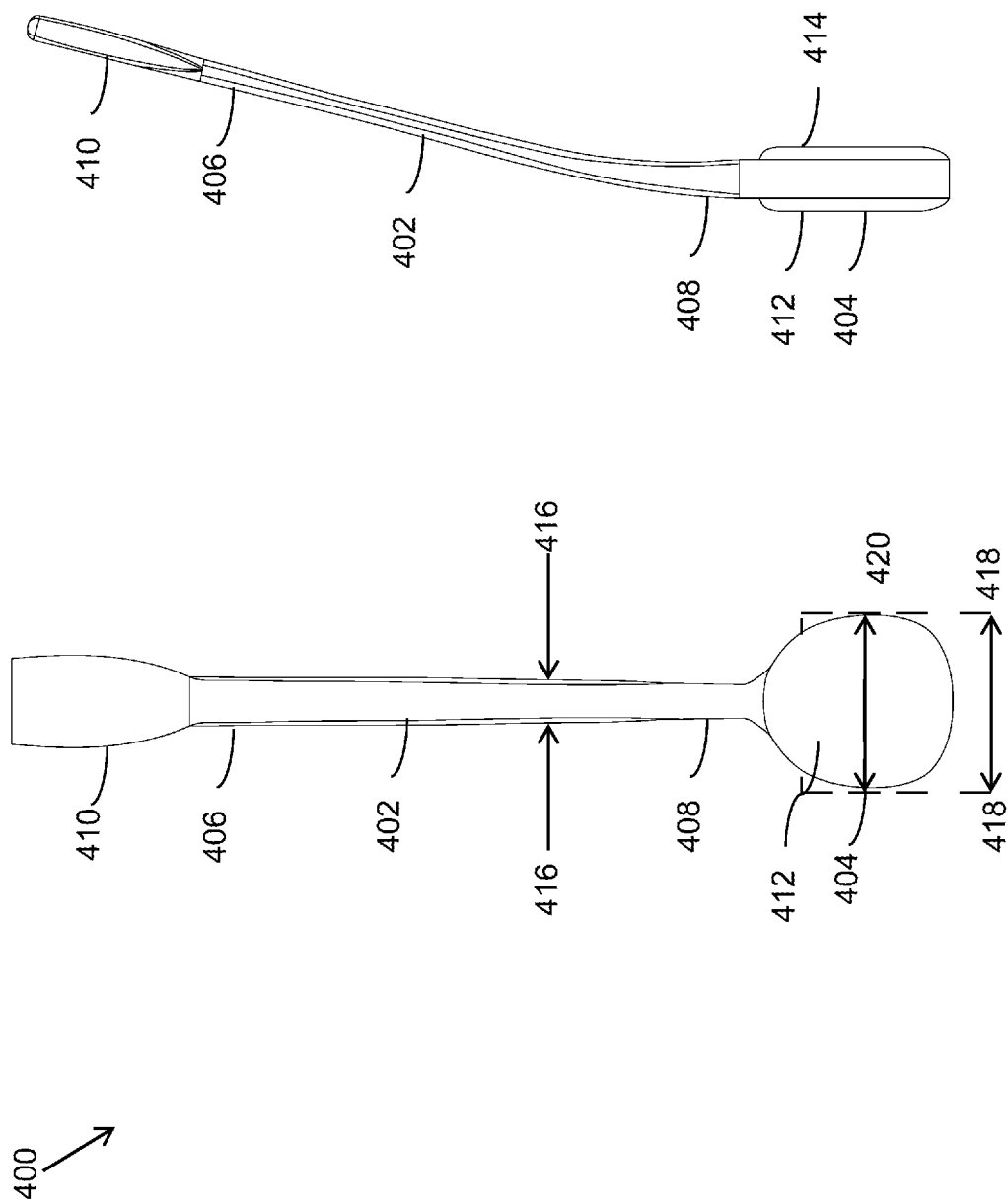

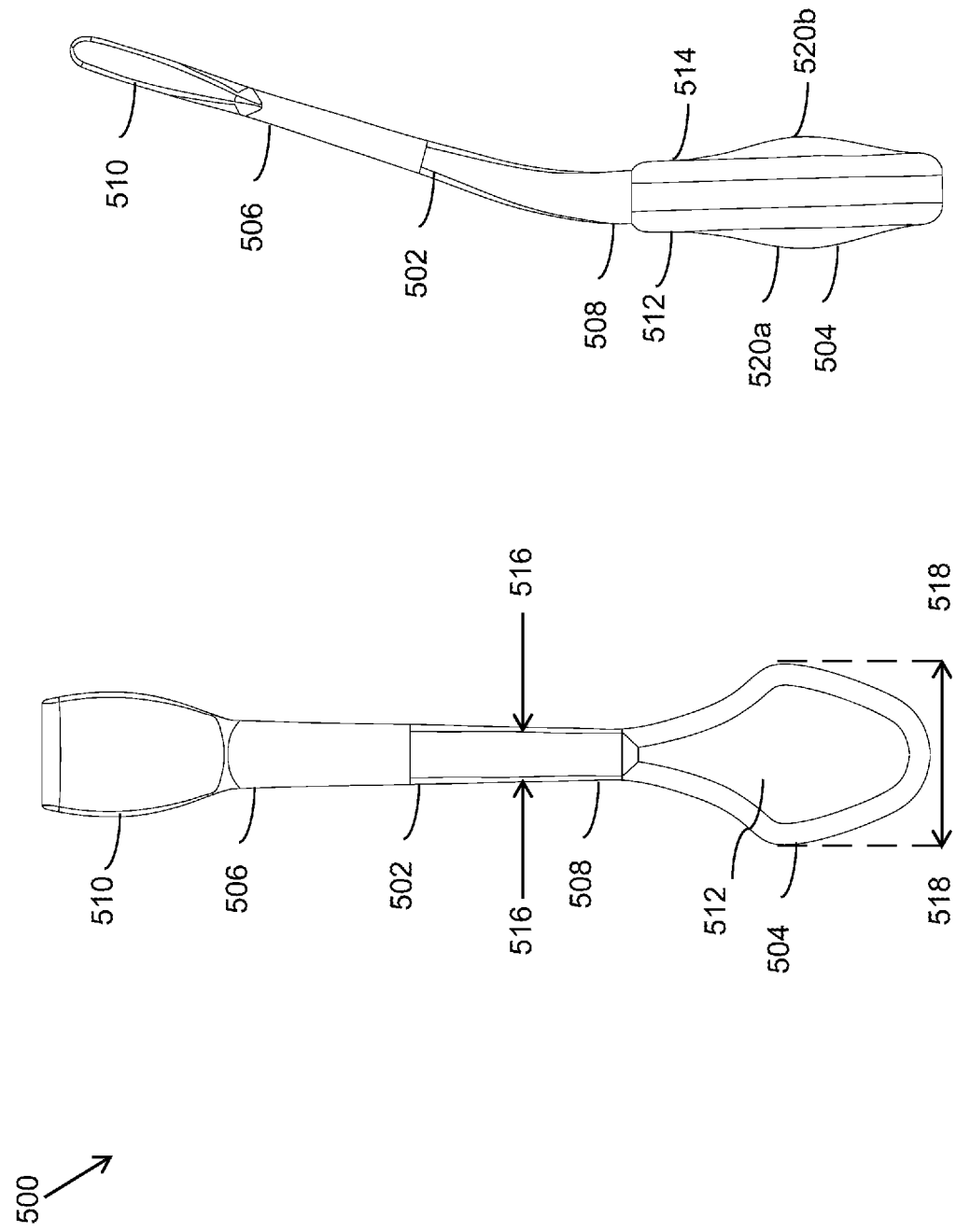

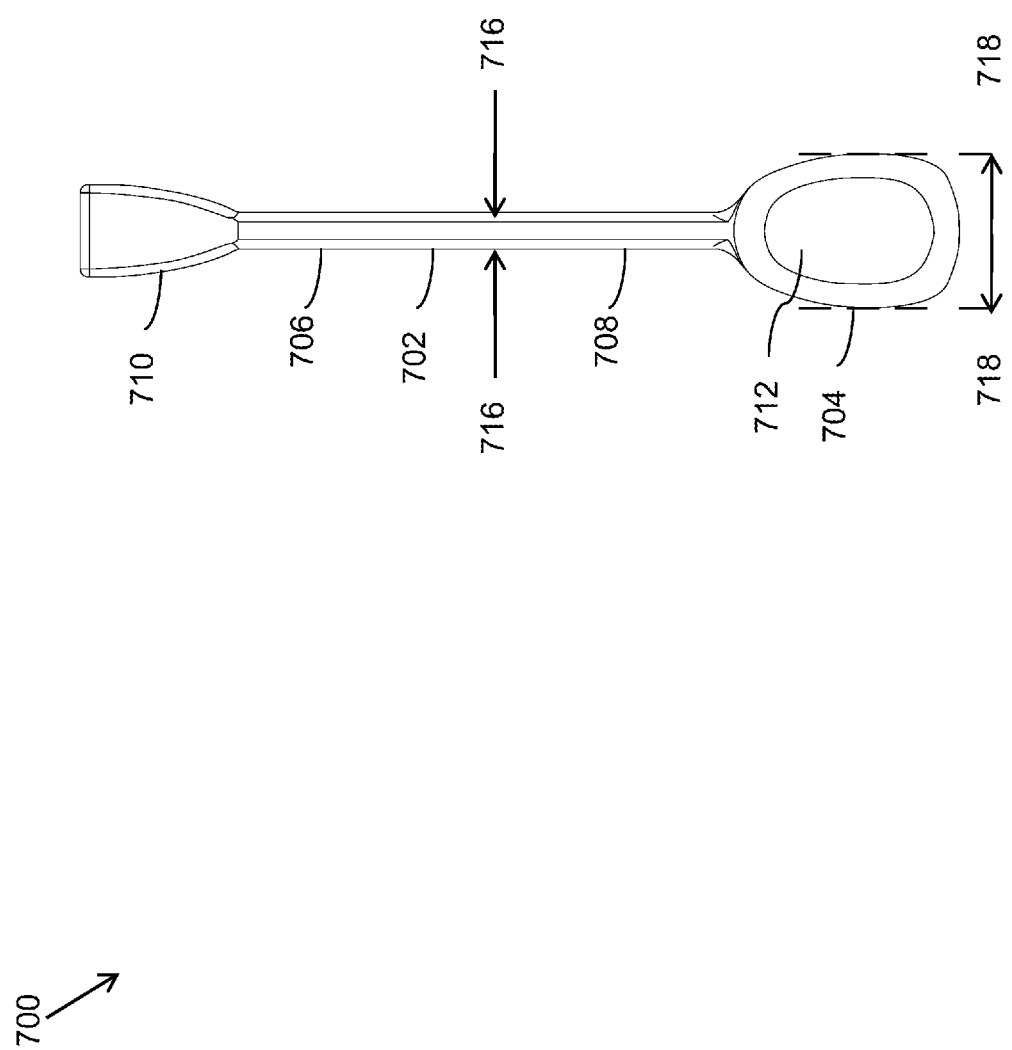

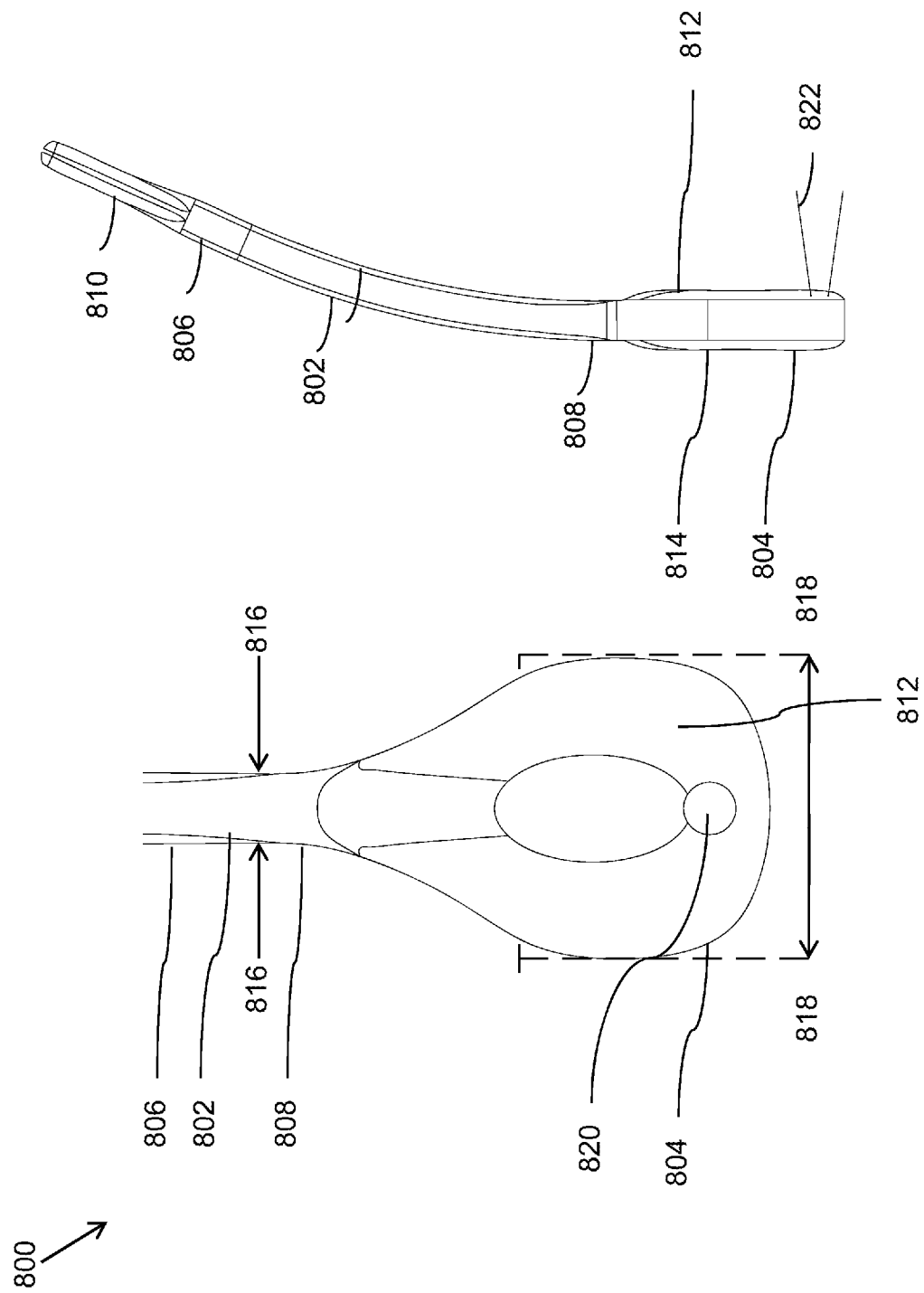

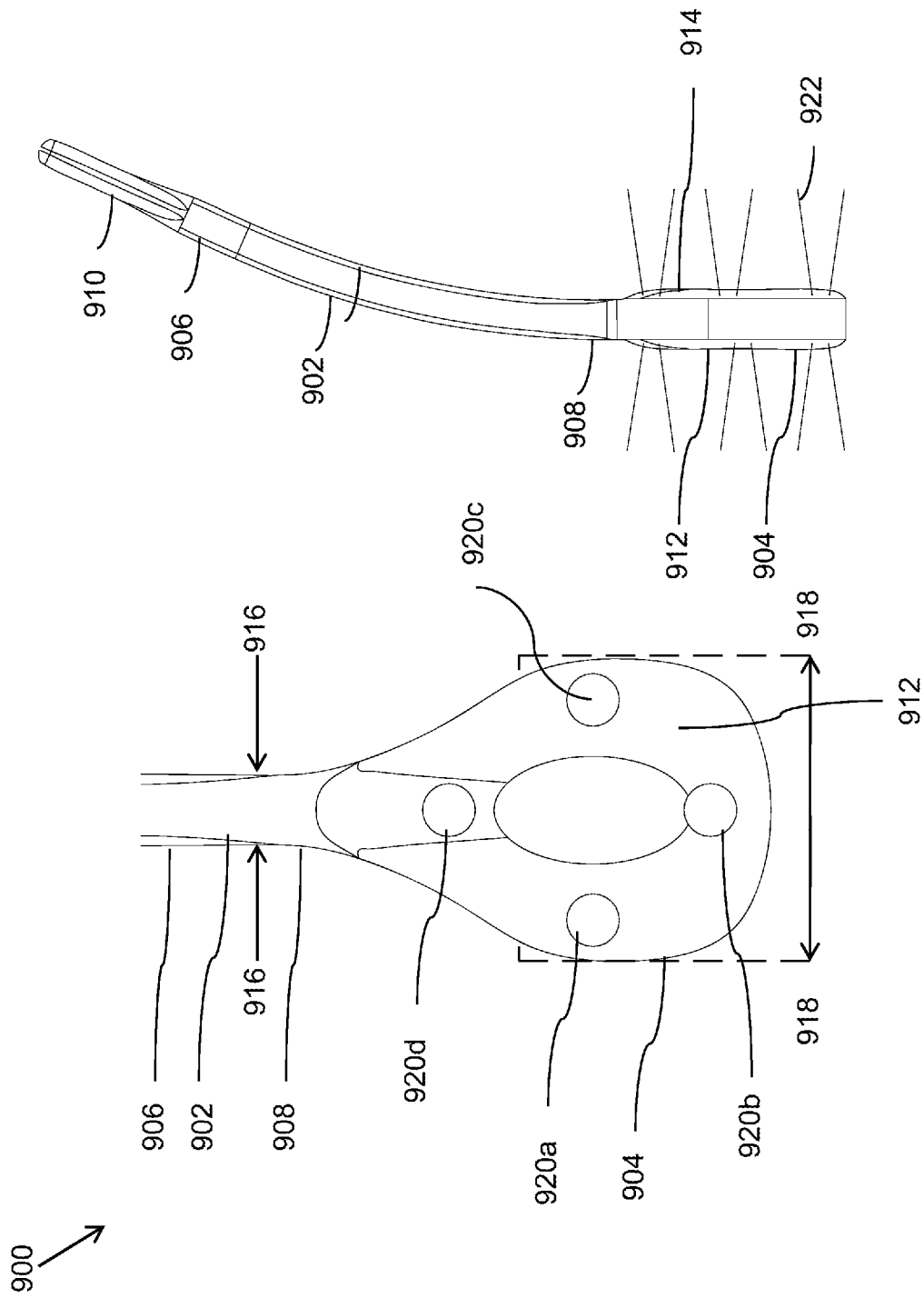

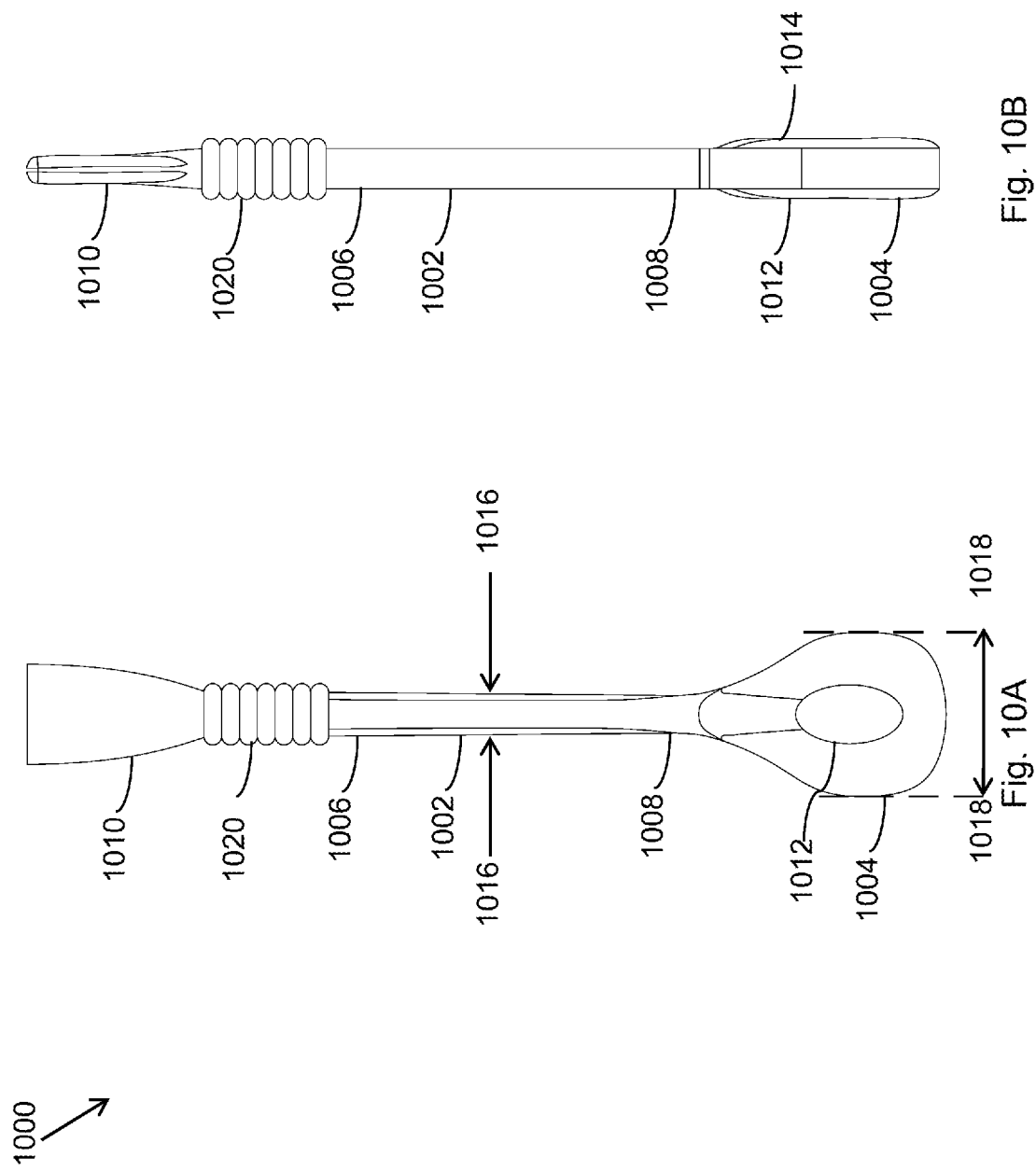

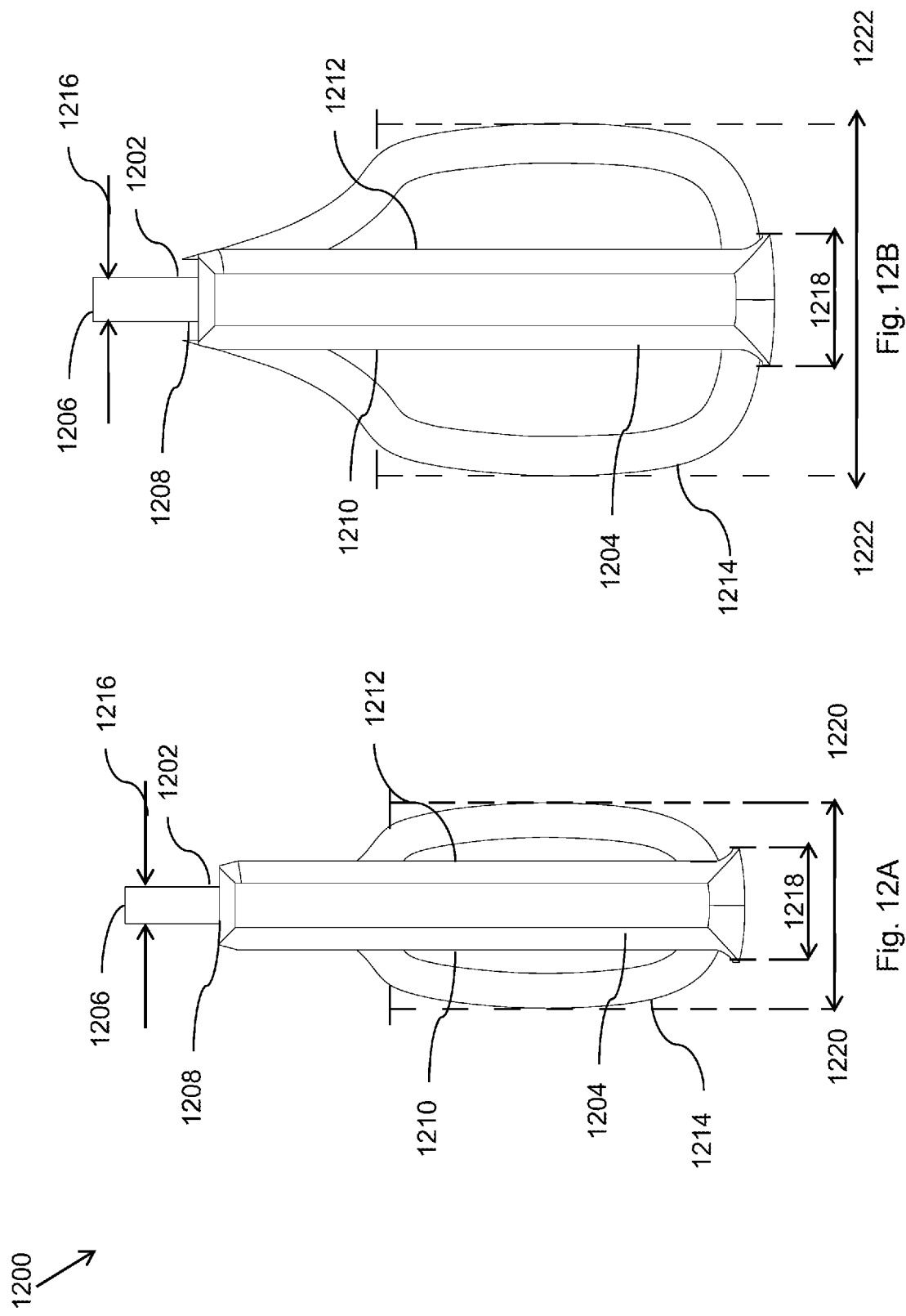

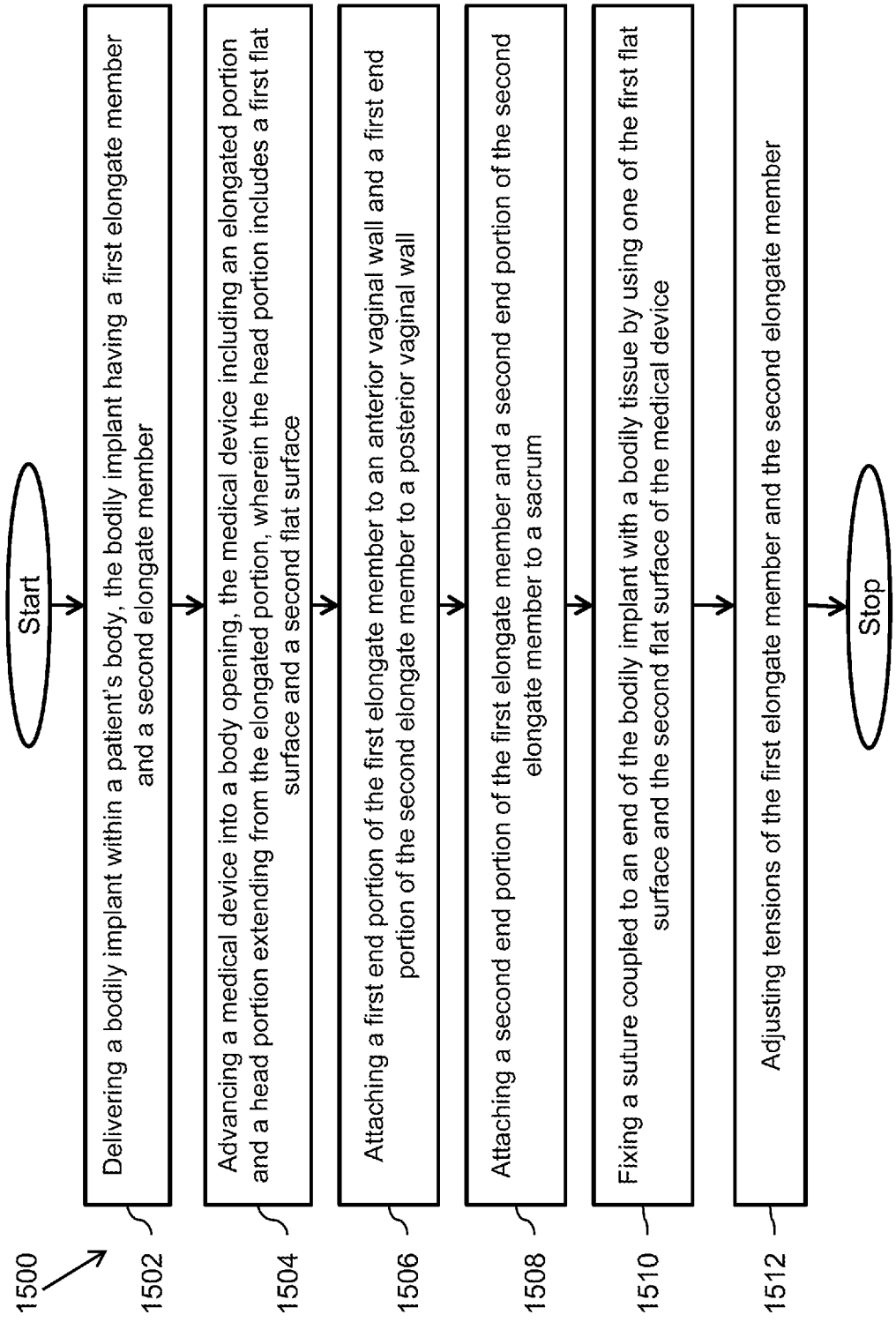

DEVICES AND METHODS FOR MANIPULATING BODILY TISSUES

CROSS-REFERENCE TO RELATED APPLICATION

This application is a Nonprovisional of, and claims priority to, U.S. Patent Application No. 61/535,095, filed Sep. 15, 2011, entitled "DEVICES AND METHODS FOR MANIPULATING BODILY TISSUES", which is incorporated by reference herein in its entirety.

BACKGROUND

Field

The present invention generally relates to medical devices and procedures, particularly devices and methods used during surgery/operation for the treatment of pelvic organ prolapse.

Various types of tissue manipulators are used for manipulating pelvic and other organs to facilitate access to their anatomical structures during surgical procedures. A vaginal manipulator is one such manipulator that can be introduced into a vagina for manipulating vaginal tissues. Several vaginal manipulators are available to help maneuver the vagina, facilitating proper dissection in the pelvis. The purpose of some vaginal manipulators is to move the vagina around so that it is easier for dissection and placement of various medical devices such as slings. The vaginal manipulator may also act as a backstop for suturing during abdominal/laparoscopic pelvic floor procedures.

Various shapes of vaginal manipulators are available to meet the requirements of surgery. Some existing manipulators used in pelvic surgeries are round or cylindrical in shape at their distal ends and are configured to contact the vaginal tissues. It can become difficult to suture the bodily tissues with these round and cylindrical shapes at the distal ends. For example, they may provide a relatively small area for manipulation and maneuvering. This can also result in the device not functioning as a positive stop during suturing applications.

Further, the anatomy of the vagina may be wide and may not be completely cylindrical. It is well known that the vagina is relatively long, hollow, and has a tube like structure that extends from the cervix or the outer end of the uterus down to the labia minora. Hence, the round or cylindrical manipulator may not be preferably shaped to cooperate with the shape of the vagina completely. As per the surgical requirements and also considering the anatomy of the vagina, the existing manipulators therefore may not be suitable to comfortably and easily repair pelvic damage. In addition, certain other features such as easy visualization and a wide range of angular manipulation of the manipulators may also be required for an efficient surgical procedure.

Thus, there is a need for an improved medical device/manipulator having a shape that suits the vaginal anatomical structure, provides easy visualization of bodily tissues during surgical processes, and can operate at a wide range of angular adjustments.

SUMMARY

A medical device and a method for manipulating bodily tissues are described. The medical device includes an elongated portion having a proximal end portion and a distal end portion. The elongated portion has a defined width referred to as first width. The medical device further includes a head portion extending from the distal end portion of the elongated portion. The head portion includes a first flat surface on a first side and a second flat surface on a second side opposite the first side. The head portion has a defined width referred to as the second width. The second width is greater than the first width.

BRIEF DESCRIPTION OF THE FIGURES

The invention and the following detailed description of certain embodiments thereof may be understood with reference to the following figures:

FIGS. 2A and 2B are the front and side views of a medical device configured to manipulate a bodily tissue, in accordance with an embodiment of the present invention.

FIGS. 3A and 3B are the front and side views of a medical device configured to manipulate a bodily tissue, in accordance with an embodiment of the present invention.

FIGS. 4A and 4B are the front and side views of a medical device configured to manipulate a bodily tissue, in accordance with an embodiment of the present invention.

FIGS. 5A and 5B are the front and side views of a medical device configured to manipulate a bodily tissue, in accordance with an embodiment of the present invention.

FIG. 7 is a front view of a medical device configured to manipulate a bodily tissue, in accordance with an embodiment of the present invention.

FIGS. 8A and 8B are the front and side views of a medical device configured to manipulate a bodily tissue, in accordance with an embodiment of the present invention.

FIGS. 9A and 9B are the front and side views of a medical device configured to manipulate a bodily tissue, in accordance with an embodiment of the present invention.

FIGS. 10A and 10B are the front and side views of a medical device configured to manipulate a bodily tissue, in accordance with an embodiment of the present invention.

FIG. 12A is a front view of a medical device in a collapsed configuration that is configured to manipulate a bodily tissue, in accordance with an embodiment of the present invention.

FIG. 12B is a front view of the medical device of FIG. 12A in an expanded configuration that is configured to manipulate a bodily tissue, in accordance with an embodiment of the present invention.

FIG. 15 illustrates a flowchart depicting a method for suturing a bodily implant within a patient's body, in accordance with an embodiment of the present invention.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

In general, the invention is directed to systems, methods, and devices for treating female pelvic prolapse. However, the invention can be equally employed for other treatment purposes such as anal prolapse in males or females. As described below in various illustrative embodiments, the invention provides systems, methods, and devices employing an improved manipulator configured to help maneuver the vagina facilitating proper dissection in the pelvis. The purpose of the vaginal manipulator is to move the vagina around so that it is easier for dissection and placement of various implants into a patient's body. The vaginal manipulator also acts as a backstop for suturing during abdominal/laparoscopic pelvic floor procedures.

The term patient may hereafter be used for a person who benefits from the medical device or the methods disclosed in the present invention. For example, the patient can be a person whose body is operated through the medical device or the method disclosed by the present invention. For example, in some embodiments, the patient may be a human female, a human male, or any other mammal.

The terms proximal and distal described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure and operate the medical device as described in the present invention. The term proximal refers to an area or portion that is closer or closest to the operator during a surgical procedure. The term distal refers to an area or portion that is farther or farthest from the operator.

Figure 1:
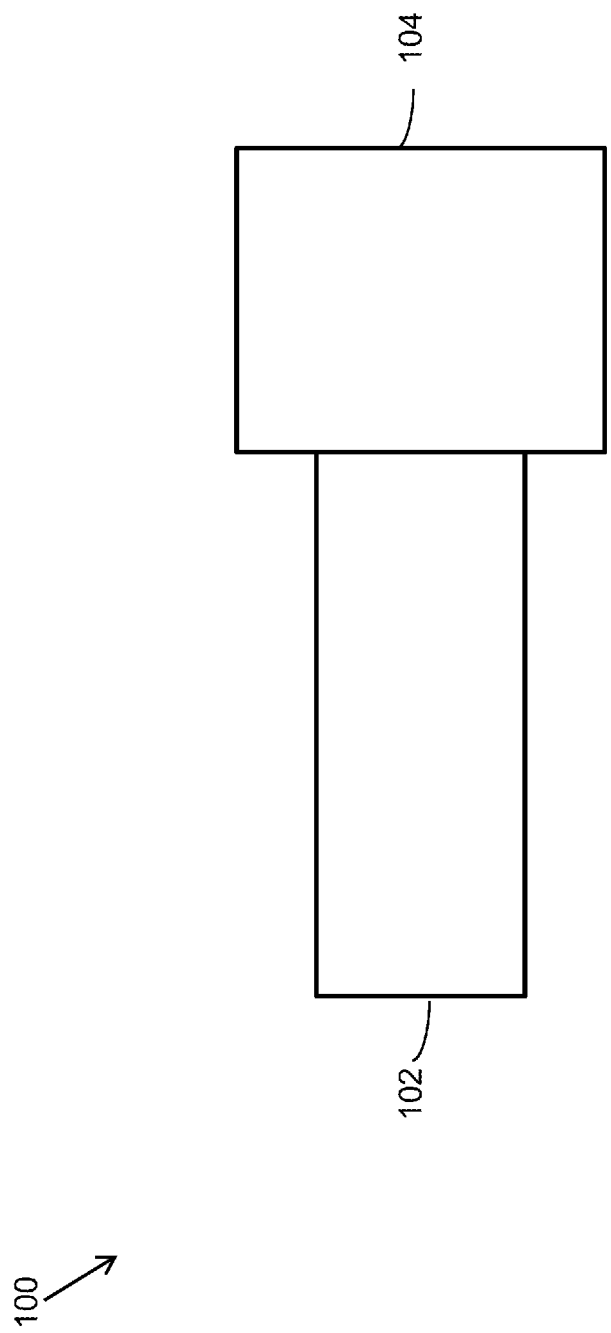
FIG. 1 is a schematic diagram of a medical device configured to manipulate a bodily tissue, in accordance with an embodiment of the present invention.

FIG. 1 is a schematic diagram of a medical device 100 configured to manipulate a bodily tissue. The medical device 100 includes an elongated portion 102 and a head portion 104 extending from the elongated portion 102. In accordance with some embodiments, the medical device 100 can be a vaginal manipulator configured to manipulate vaginal tissues.

The elongated portion 102 includes a proximal end portion and a distal end portion. The elongated portion 102 has a predefined width referred to as first width. The elongated portion 102 may also include a handle at its proximal end portion ergonomically designed to be gripped by an operator or a surgeon. In certain embodiments, the elongated portion 102 may be cylindrical in shape having a circular cross section at the distal end portion and the proximal end portion. In other embodiments, the elongated portion 102 may be shaped such that the cross section is rectangular, or square, or any other shape at its distal end portion and the proximal end portion. Similarly, various other shapes of the elongated portion 102 are possible. For example, the cross section of the proximal end portion and the distal end portion can be pentagonal, hexagonal, octal, and the like. In accordance with some embodiments, the width of the elongated portion 102 is uniform from the proximal end portion to the distal end portion. In accordance with other embodiments, the elongated portion 102 may be tapered having the first width at the distal end portion. In some embodiments, the elongated portion 102 is flexible in nature. In other embodiments, the elongated portion 102 is rigid.

The head portion 104 extends from the distal end portion of the elongated portion 102. The head portion 104 has a second width such that the second width is greater than the first width (of the elongated portion 102). In this manner, the head portion 104 projects/bulges laterally from the elongated portion 102 and provides even a larger surface area for tissue manipulation through the head portion 104.

The head portion 104 includes a first flat surface on a first side of the head portion 104 and a second flat surface on a second side opposite the first side. In some embodiments, the first flat surface and the second flat surface have greater width than the first width (of the elongated portion 102). In some embodiments, the first flat surface and the second flat surface have width equal to the width of the head portion (second width). The first flat surface and the second flat surface are configured to provide a larger surface for manipulation of the bodily tissues such as the vaginal tissues. This helps maneuver the vagina to facilitate proper dissection in the pelvis. The purpose of the flat surfaces of the vaginal manipulator is to move the vagina around so that it is easier for dissection and placement of implants such as slings. The first flat surface and the second flat surface also act as a backstop for suturing during abdominal/laparoscopic pelvic floor procedures. The first flat surface and the second flat surface can also be used to spread the bodily tissue to facilitate suturing at a correct location. It must be appreciated that either of the first flat surface and the second flat surface can be used one at a time for manipulation. In some embodiments, the surgeon/operator may use the first flat surface to suture on anterior portions of the vagina and the second flat surface to suture on posterior portions of the vagina.

In certain embodiments, the head portion 104 and the elongated portion 102 form an integral part of the complete medical device 100. In some other embodiments, the elongated portion 102 and the head portion 104 can be removably attached with one another. The head portion 104 can be coupled to the elongated portion 102 through welds, arms, prongs, clips, and other fastening mechanisms.

In some embodiments, the coupling/attachment of the head portion 104 with the elongated portion 102 may not allow relative motion between them. In other embodiments, the elongated member 102 can be coupled to the head portion 104 through a pivot joint such that relative motion between the head portion 104 and the elongated portion 102 is possible. This may assist in manipulation of the bodily tissues.

FIGS. 2A and 2B illustrate the front and side views of a medical device 200 configured to manipulate a bodily tissue, in accordance with an embodiment of the present invention. The medical device 200 includes an elongated portion 202 and a head portion 204 extending from the elongated portion 202. In accordance with some embodiments, the medical device 200 can be a vaginal manipulator configured to manipulate vaginal tissues.

The elongated portion 202 includes a proximal end portion 206 and a distal end portion 208. The elongated portion 202 has a defined width referred to as a first width 216. The elongated portion 202 may also include a handle 210 at its proximal end portion 206 ergonomically designed to be gripped by an operator or a surgeon. In some embodiments, the elongated portion 202 is made of a flexible material. In other embodiments, the elongated portion 202 is made of a rigid material.

The head portion 204 extends from the distal end portion 208 of the elongated portion 202. The head portion 204 has a second width 218 such that the second width 218 is greater than the first width 216 (of the elongated portion 202). In this manner, the head portion 204 projects/bulges laterally from the elongated portion 202 and provides even a larger surface area for tissue manipulation through the head portion 204. As illustrated in FIG. 2A, the head portion 204 may include a hole in the center. However, in accordance with other embodiments, the head portion 204 may be completely filled with material (without a hole).

The head portion 204 includes a first flat surface 212 on a first side of the head portion 204 and a second flat surface 214 on a second side opposite the first side. In some embodiments, the first flat surface 212 and the second flat surface 214 have greater width than the first width 216 (of the elongated portion 202). In some embodiments, the first flat surface 212 and the second flat surface 214 have width equal to the width of the head portion 204 (second width 218). The first flat surface 212 and the second flat surface 214 are configured to provide a larger surface for manipulation of bodily tissues such as the vaginal tissues. This helps maneuver the vagina facilitating proper dissection in the pelvis. The purpose of the flat surfaces 212 and 214 of the medical device 200 is to move the vagina around so that it is easier for dissection and placement of implants such as slings. The first flat surface 212 and the second flat surface 214 also act as a backstop for suturing during abdominal/laparoscopic pelvic floor procedures. The first flat surface 212 and the second flat surface 214 can also be used to spread the bodily tissue to facilitate suturing at a correct location. It must be appreciated that either or both of the first flat surface 212 and the second flat surface 214 can be used one at a time for manipulation.

In certain embodiments, the head portion 204 and the elongated portion 202 form an integral part of the complete medical device 200. In some other embodiments, the elongated portion 202 and the head portion 204 can be removably attached with one another. The head portion 204 can be coupled to the elongated portion 202 through welds, arms, prongs, clips, and other fastening mechanisms.

In some embodiments, the coupling/attachment of the head portion 204 with the elongated portion 202 does not allow any relative motion. In other embodiments, the elongated portion 202 can be coupled to the head portion 204 through a pivot joint such that a relative motion between the head portion 204 and the elongated portion 202 is possible. This may assist in manipulation of the bodily tissues.

The shape of the elongated portion 202 and the head portion 204 described in conjunction with FIG. 2 is merely exemplary and various other shapes are also possible such as those illustrated in conjunction with FIGS. 3A-6.

FIGS. 3A and 3B illustrate the front and side views of a medical device 300 configured to manipulate a bodily tissue, in accordance with another embodiment of the present invention. The medical device 300 includes an elongated portion 302 and a head portion 304 extending from the elongated portion 302. As illustrated in FIG. 3A, the head portion 304 is greater in width than the elongated portion 302 to ensure increased surface area contact between the head portion 304 and the bodily tissue. The elongated portion 302 is roughly a narrow extension extending from the head portion 304. The head portion 304 may be roughly bulbous with a substantially circular or oval shape along its sides. The bulbous shape of the head portion 304 is similar to the shape of a light bulb bulging on either sides as compared to the elongated portion 302, and having a slightly flat portion at its distal and proximal ends. The head portion 304 includes a first flat surface 312 on a first side of the head portion 304 and a second flat surface 314 on a second side opposite the first side. In some embodiments, the first flat surface 312 and the second flat surface 314 have greater width than the first width 316 (of the elongated portion 302). As an exemplary embodiment, the width of the first flat surface 312 and the second flat surface 314 is depicted as 320. The second flat surface 314 is hidden in this view and therefore its width cannot be seen. In some other embodiments, the width of the first flat surface 312 may be different from the width of the second flat surface 314. As illustrated, the width 320 of the first flat surface 312 and the second flat surface 314 is not equal to (lesser than) the width 318 of the head portion 304.

FIGS. 4A and 4B illustrate the front and side views of a medical device 400 configured to manipulate a bodily tissue, in accordance with another embodiment of the present invention. The medical device 400 includes an elongated portion 402 and a head portion 404 extending from the elongated portion 402. As illustrated in FIG. 4A, the head portion 404 is greater in width than the elongated portion 402 to ensure increased surface area contact between the head portion 404 and the bodily tissue. The elongated portion 402 is roughly a narrow extension extending from the head portion 404. The head portion 404 may be roughly bulbous with a substantially circular or oval shape along its sides. The bulbous shape of the head portion 404 is similar to the shape of a light bulb bulging on either sides as compared to the elongated portion 402, and having a slightly flat portion at its distal and proximal ends. The head portion 404 includes a first flat surface 412 on a first side of the head portion 404 and a second flat surface 414 on a second side opposite the first side. In some embodiments, the first flat surface 412 and the second flat surface 414 have greater width than the first width 416 (of the elongated portion 402). As an exemplary embodiment, the width of the first flat surface 412 and the second flat surface 414 is depicted as 420. The second flat surface 414 is hidden in this view and therefore its width cannot be seen. In some other embodiments, the width of the first flat surface 412 may be different from the width of the second flat surface 414. As illustrated, the width 420 of the first flat surface 412 and the second flat surface 414 is equal to the width 418 of the head portion 404 in the illustrated embodiment. The first flat surface 312 and the second flat surface 314 are configured to provide a larger surface for manipulation of bodily tissues such as the vaginal tissues.

FIGS. 5A and 5B illustrate the front and side views of a medical device 500 configured to manipulate a bodily tissue, in accordance with another embodiment of the present invention. The medical device 500 includes an elongated portion 502 and a head portion 504 extending from the elongated portion 502. As illustrated in FIG. 5A, the head portion 504 is greater in width than the elongated portion 502 to ensure increased surface area contact between the head portion 504 and the bodily tissue. The elongated portion 502 is roughly a narrow extension extending from the head portion 504. The head portion 504 tapers from its proximal end portion (coupled to the elongated portion 502) and the distal end portion toward the middle portion such that the width of the head portion 504 is maximum at the middle portion. The distal end of the head portion 504 can be roughly pointed. The head portion 504 includes a first flat surface 512 on a first side of the head portion 504 and a second flat surface 514 on a second side opposite the first side. In some embodiments, the first flat surface 512 and the second flat surface 514 have greater width than the first width 516 (of the elongated portion 502). In some embodiments, the first flat surface 512 and the second flat surface 514 have width equal to the width of the head portion 504 (second width 518). The first flat surface 512 and the second flat surface 514 are configured to provide a larger surface for manipulation of bodily tissues such as the vaginal tissues. In some embodiments, lateral edges of the head portion 504 can be shaped to bulge out in the middle as shown by humped portions 520a and 520b on either lateral sides of the head portion 504 in FIG. 5B. In some other embodiments, the head portion 504 can bulge out on transverse edges as well.

Figure 6B:
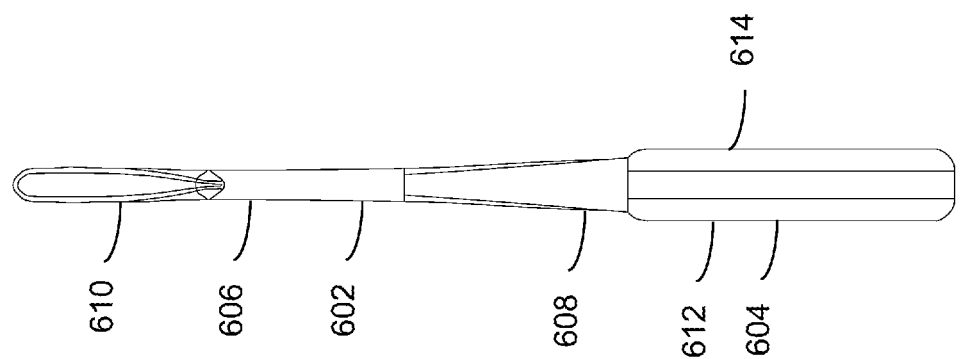
FIGS. 6A and 6B are the front and side views of a medical device configured to manipulate a bodily tissue, in accordance with an embodiment of the present invention.
Figure 6A:
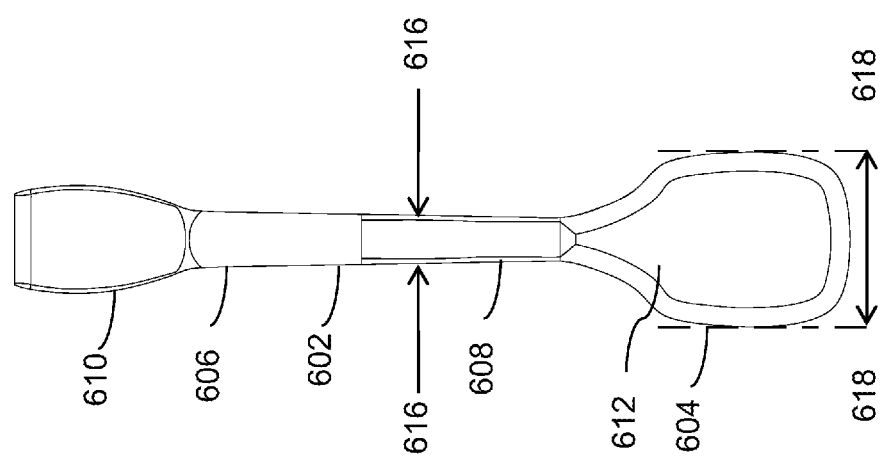

FIGS. 6A and 6B illustrate the front and side views of a medical device 600 configured to manipulate a bodily tissue, in accordance with another embodiment of the present invention. The medical device 600 includes an elongated portion 602 and a head portion 604 extending from the elongated portion 602. As illustrated in FIG. 6A, the head portion 604 is greater in width than the elongated portion 602 to ensure increased surface area contact between the head portion 604 and the bodily tissue. The elongated portion 602 is roughly a narrow extension extending from the head portion 604. As illustrated in FIG. 6A, the head portion 604 tapers from its proximal end portion toward its middle portion such that the width of the head portion 604 is maximum at the middle portion. The portion between the middle and the distal locations of the head portion 604 has the same width in this case. The distal end of the head portion 604 is substantially rectangular and provides a large area of contact. The head portion 604 includes a first flat surface 612 on a first side of the head portion 604 and a second flat surface 614 on a second side opposite the first side. In some embodiments, the first flat surface 612 and the second flat surface 614 have width greater than the first width 616 (of the elongated portion 602). In some embodiments, the first flat surface 612 and the second flat surface 614 have width equal to the width of the head portion 604 (second width 618). The first flat surface 612 and the second flat surface 614 are configured to provide a larger surface for manipulation of bodily tissues such as the vaginal tissues.

FIG. 7 illustrates the front view of a medical device 700 configured to manipulate a bodily tissue, in accordance with another embodiment of the present invention. The medical device 700 includes an elongated portion 702 and a head portion 704 extending from the elongated portion 702. As illustrated in FIG. 7, the head portion 704 is greater in width than the elongated portion 702 to ensure increased surface area contact between the head portion 704 and the bodily tissue. The elongated portion 702 is roughly a narrow extension extending from the head portion 704. As illustrated in FIG. 7, the head portion 704 is substantially circular/oval along its sides and has a bulbous shape. The bulbous shape of the head portion 704 is similar to the shape of a light bulb bulging on either sides as compared to the elongated portion 702, and having a slightly flat portion at its distal and proximal ends. The distal end of the head portion 704 can be substantially flat or slightly pointed. The head portion 704 includes a first flat surface 712 on a first side of the head portion 704 and a second flat surface 714 on a second side opposite the first side. In some embodiments, the first flat surface 712 and the second flat surface 714 have greater width than the first width 716 (of the elongated portion 702). In some embodiments, the first flat surface 712 and the second flat surface 714 have width equal to the width of the head portion 704 (second width 718). The first flat surface 712 and the second flat surface 714 are configured to provide a larger surface for manipulation of bodily tissues such as the vaginal tissues.

In accordance with various other embodiments, various other shapes of the head portions and the elongated portions are also possible.

FIGS. 8A and 8B are the front and side views of a medical device 800 configured to manipulate a bodily tissue. The medical device 800 includes an elongated portion 802 and a head portion 804 extending from the elongated portion 802. In accordance with some embodiments, the medical device 800 can be a vaginal manipulator configured to manipulate vaginal tissues.

The elongated portion 802 includes a proximal end portion 806 and a distal end portion 808. The elongated portion 802 has a defined width referred to as a first width 816. The elongated portion 802 can also include a handle 810.

The head portion 804 extends from the distal end portion 808 of the elongated portion 802. The head portion 804 has a second width 818 such that the second width 818 is greater than the first width 816 (of the elongated portion 802). The head portion 804 includes a first flat surface 812 on a first side of the head portion 804 and a second flat surface 814 on a second side opposite the first side. The first flat surface 812 and the second flat surface 814 are configured to provide a larger surface for manipulation of the bodily tissues such as the vaginal tissues. The elongated portion 802 and the head portion 804 have been discussed in conjunction with FIGS. 1 and 2 in detail.

In accordance with this embodiment, the head portion 804 includes a light source 820. The light source 820 is configured to project light through a bodily tissue such as a vaginal tissue that is being operated during the surgery. In some embodiments, the light source 820 is disposed and fitted on the first flat surface 812. In some other embodiments, the light source 820 is disposed and fitted on the second flat surface 814. In some other embodiments, the light source 820 is disposed on both the first flat surface 812 and the second flat surface 814.

In some embodiments, the light source 820 emits light that is different from the white light. For example, the light color can be blue. The non-white light such as blue light may assist in the visualization through the bodily tissue where the flat surfaces 212 and 214 operate during surgery and inspection. FIG. 8A illustrates the use of one light source 820 for projecting light 822 through the bodily tissue. However, in other embodiments, a medical device such as the medical device 900 of FIGS. 9A and 9B may include more than one light source. FIGS. 9A and 9B are the front and side views of the medical device 900 having more than one light sources. FIG. 9A illustrates the use of four light sources 920a, 920b, 920c, and 920d.

FIGS. 10A and 10B are the front and side views of a medical device 1000 configured to manipulate a bodily tissue, in accordance with an embodiment of the present invention.

The medical device 1000 includes an elongated portion 1002 and a head portion 1004 extending from the elongated portion 1002. In accordance with some embodiments, the medical device 1000 can be a vaginal manipulator configured to manipulate vaginal tissues.

The elongated portion 1002 includes a proximal end portion 1006 and a distal end portion 1008. The elongated portion 1002 has a defined width referred to as a first width 1016. The elongated portion 1002 can also include a handle 1010.

The head portion 1004 extends from the distal end portion 1008 of the elongated portion 1002. The head portion 1004 has a second width 1018 such that the second width 1018 is greater than the first width 1016 (of the elongated portion 1002). The head portion 1004 includes a first flat surface 1012 on a first side of the head portion 1004 and a second flat surface 1014 on a second side opposite the first side. The first flat surface 1012 and the second flat surface 1014 are configured to provide a larger surface for manipulating the bodily tissues such as the vaginal tissues. The elongated portion 1002 and the head portion 1004 have been discussed in conjunction with FIGS. 1 and 2 in detail.

In accordance with this embodiment, the elongated portion 1002 further includes an articulating member 1020. The articulating member 1020 is coupled to the elongated portion 1002 such that the elongated portion 1002 is configured to move about the articulating member 1020. The movement of the elongated portion 1002 through the articulating member 1020 provides an ability to alter angle of the distal end portion 1008 of the elongated portion 1002 and the head portion 1004 with respect to the proximal end portion 1006. This improves the range of motion for the bodily tissue during surgery and/or inspection. In accordance with some embodiments, a universal joint may be employed in the articulating member 1020 to provide it an articulating functionality. In other embodiments, a ball joint may be used for articulation purposes. The articulating member 1020 can be set at a desired angle by twisting it. In some embodiments, the articulating member 1020 may also include elements such as springs that facilitate to retain the angled position till the time an external force to readjust or regain the normal shape is applied. In some embodiments, the articulating member 1020 can be made of a malleable material such that it can be easily stretched during articulation. Several other types of mechanisms may be employed for articulation.

Figure 11B:
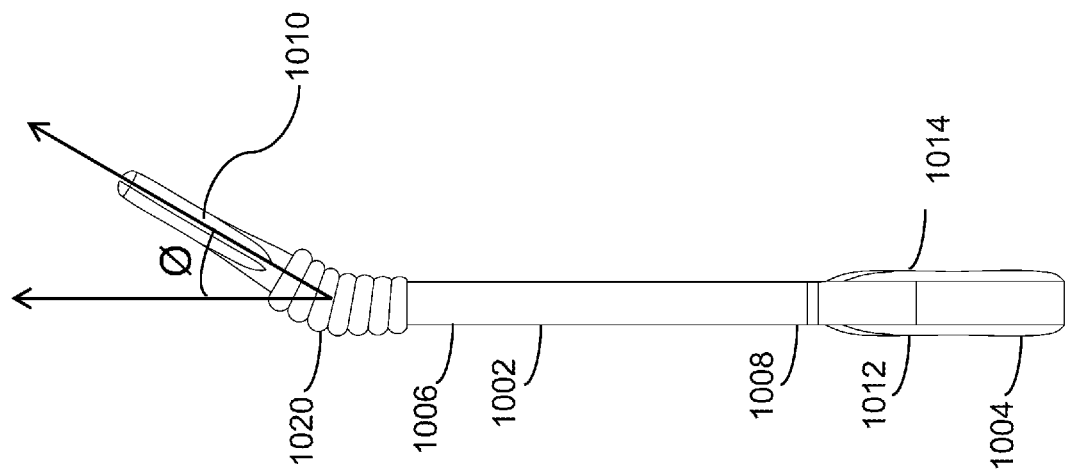
FIGS. 11A and 11B are the front and side views of a medical device configured to manipulate a bodily tissue, in accordance with an embodiment of the present invention.
Figure 11A:
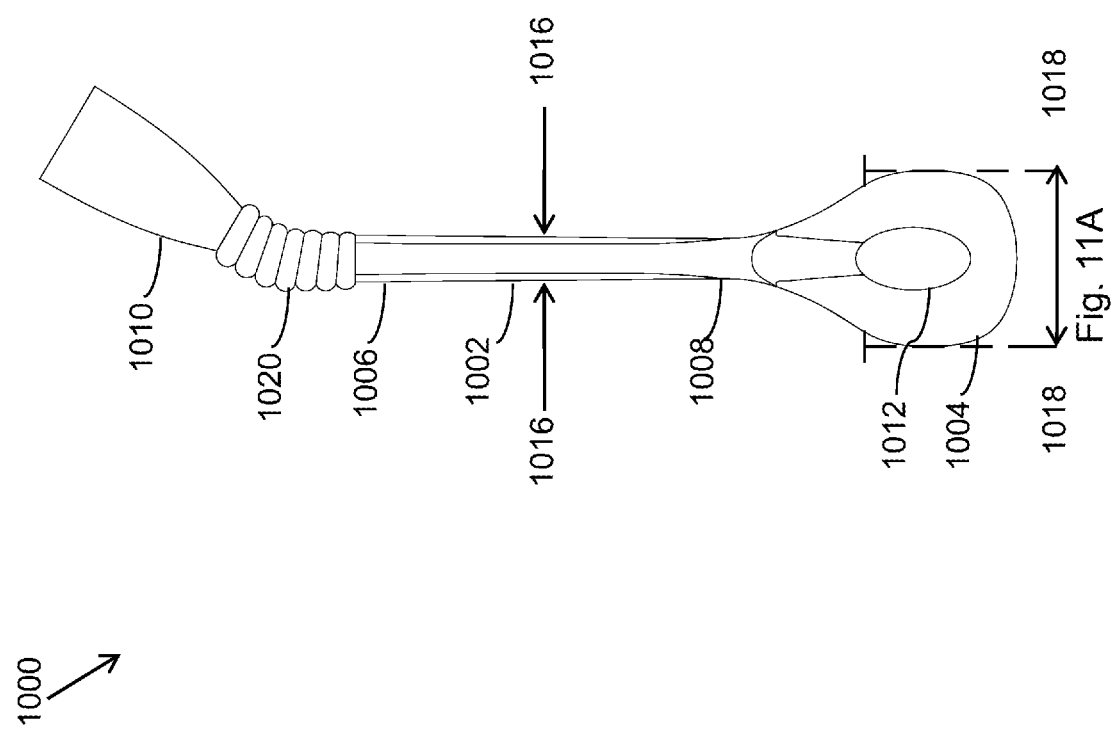

FIGS. 10A and 10B illustrate the front and side views of the medical device 1000 in a normal configuration. FIGS. 11A and 11B illustrate the front and side views of the medical device 1000 of FIGS. 10A and 10B in an articulated configuration. As illustrated in FIG. 11B, the medical device is articulated by an angle Ø toward the right side with respect to the normal axis of the elongated portion 1002. However, in certain other embodiments, the angle of articulation can vary and articulation can be done on either sides of the elongated portion 1002.

FIGS. 12A and 12B are the front and side views of a medical device 1200 configured to manipulate a bodily tissue, in accordance with an embodiment of the present invention. The medical device 1200 includes an elongated portion 1202 and a head portion 1204 extending from the elongated portion 1202. In accordance with some embodiments, the medical device 1200 can be a vaginal manipulator configured to manipulate vaginal tissues.

The elongated portion 1202 includes a proximal end portion 1206 and a distal end portion 1208. The elongated portion 1202 has a defined width referred to as a first width 1216. The head portion 1204 extends from the distal end portion 1208 of the elongated portion 1202. The head portion 1204 has a second width 1218 such that the second width 1218 is greater than the first width 1216 (of the elongated portion 1202). The head portion 1204 includes a first flat surface 1210 on a first side of the head portion 1204 and a second flat surface 1212 on a second side opposite the first side. The first flat surface 1210 and the second flat surface 1212 are configured to provide a larger surface for manipulation of the bodily tissues such as the vaginal tissues. The elongated portion 1202 and the head portion 1204 have been described in conjunction with FIGS. 1 and 2.

In accordance with this embodiment, the medical device 1200 further includes an expandable member 1214. The expandable member 1214 is coupled to the head portion 1204 and is configured to expand once the medical device 1200 is disposed inside a body opening such as a vagina, anal canal, and the like. A collapsed configuration of the expandable member 1214 is shown in FIG. 12A. An expanded configuration of the expandable member 1214 (achieved after being placed inside the body opening) is shown in FIG. 12B. As shown in FIGS. 12A and 12B, the width 1220 of the expandable member 1214 before expansion is lesser than the width 1222 after expansion. The relative difference between the width 1220 and the width 1222 can be set by the operator based on the surgical requirements such as based on the stretching required to separate a bodily tissue inside the vagina.

In some embodiments, the expandable member 1214 can include a set of flaps (not shown) such as two flaps for example. The flaps are configured to contact one another in a collapsed configuration and detach from one another in an expanded configuration. In such cases, the movement of the flaps or pieces may cause expansion or collapse of the expandable member 1214. In some other embodiments, the expandable member 1214 can include an inflatable member or membrane (not shown) such that the inflatable member/membrane controls expansion or collapse of the expandable member 1214. The expansion of the expandable member 1214 causes the body tissue to expand and provide a space for an operator to comfortably work on the bodily tissues during surgery or inspection.

In some embodiments, the head portion 1204 including the flat surfaces 1210 and 1212 is also configured to extend to edges of the expandable member 1214 such that the surface area of the flat surfaces 1210 and 1202 is increased upon extension. Therefore, the desired surface area for manipulation may be provided based on surgical requirements. In accordance with these embodiments, a panel or a similar device may be provided on the head portion 1204 so that the panel extends to increase the surface area as and when there is an expansion in the expandable member 1204.

Figure 13:
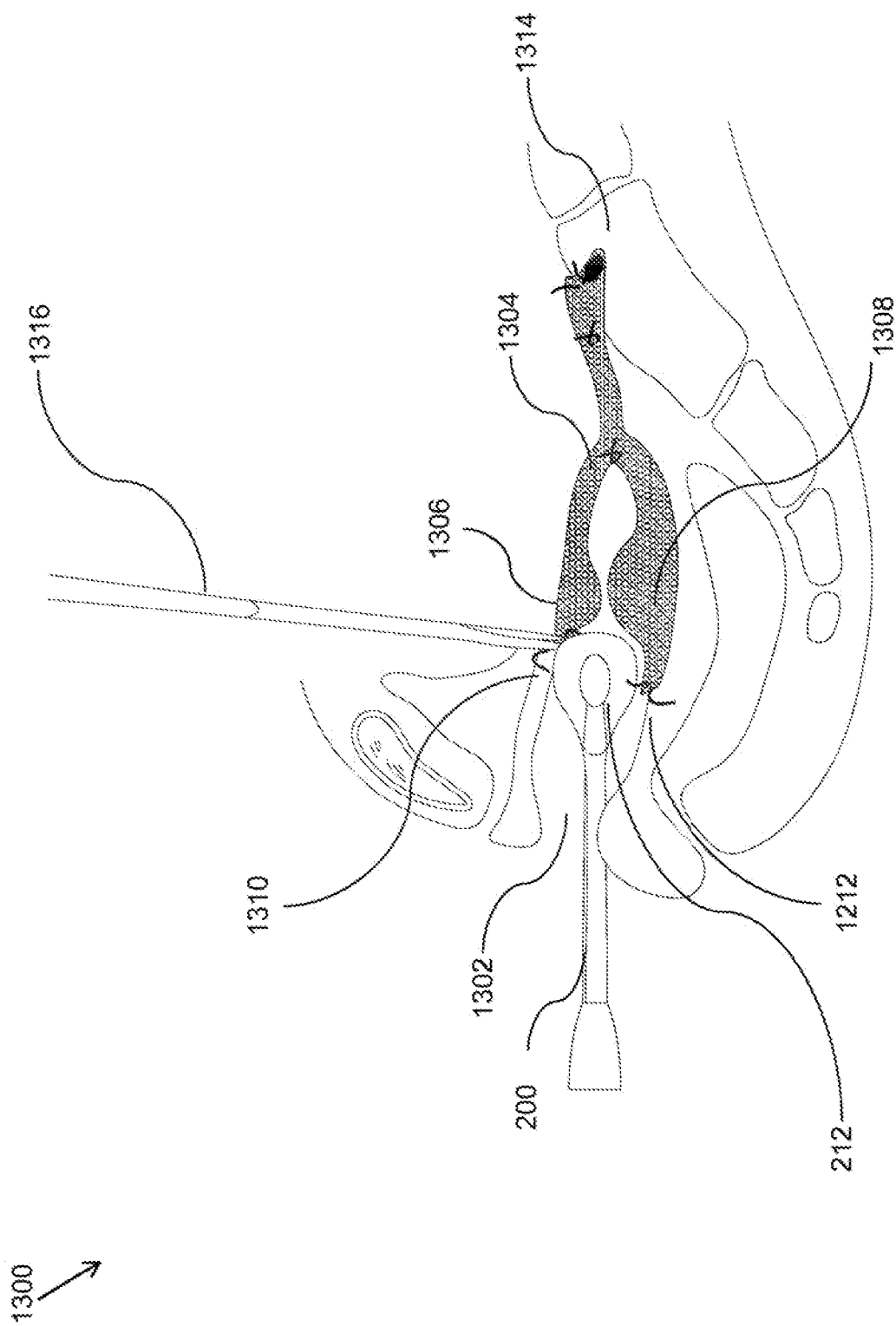
FIG. 13 illustrates placement of a medical device inside a body opening for manipulation, in accordance with an embodiment of the present invention.

FIG. 13 illustrates placement 1300 of the medical device 200 inside a vagina 1302 for manipulation of bodily tissues. As shown, one of the flat surfaces (e.g., first flat surface 212 or second flat surface) can be used to manipulate the tissues. The flat surfaces assist in moving the vagina 1302 around so that it is easier for dissection and placement of a bodily implant 1304 into a patient's body. The flat surfaces also act as a backstop for suturing during abdominal/laparoscopic pelvic floor procedures. The first flat surface 212 and the second flat surface can also be used to spread the bodily tissue to facilitate suturing at a correct location. In some embodiments, the implant 1304 includes a first elongated member 1306 and a second elongated member 1308. A first end portion of the first elongated member 1306 is attached to an anterior vaginal wall 1310 and a second end portion of the first elongated member 1306 is attached to a sacrum 1314. A first end portion of the second elongated member 1308 is attached to a posterior vaginal wall 1212 and a second end portion of the second elongated member 1308 is attached to the sacrum 1314. Additionally, a delivery device 1316 configured to make incisions and hold a suture during surgery is also depicted. In some embodiments, the delivery device 1316 can be a surgical needle.

Figure 14:
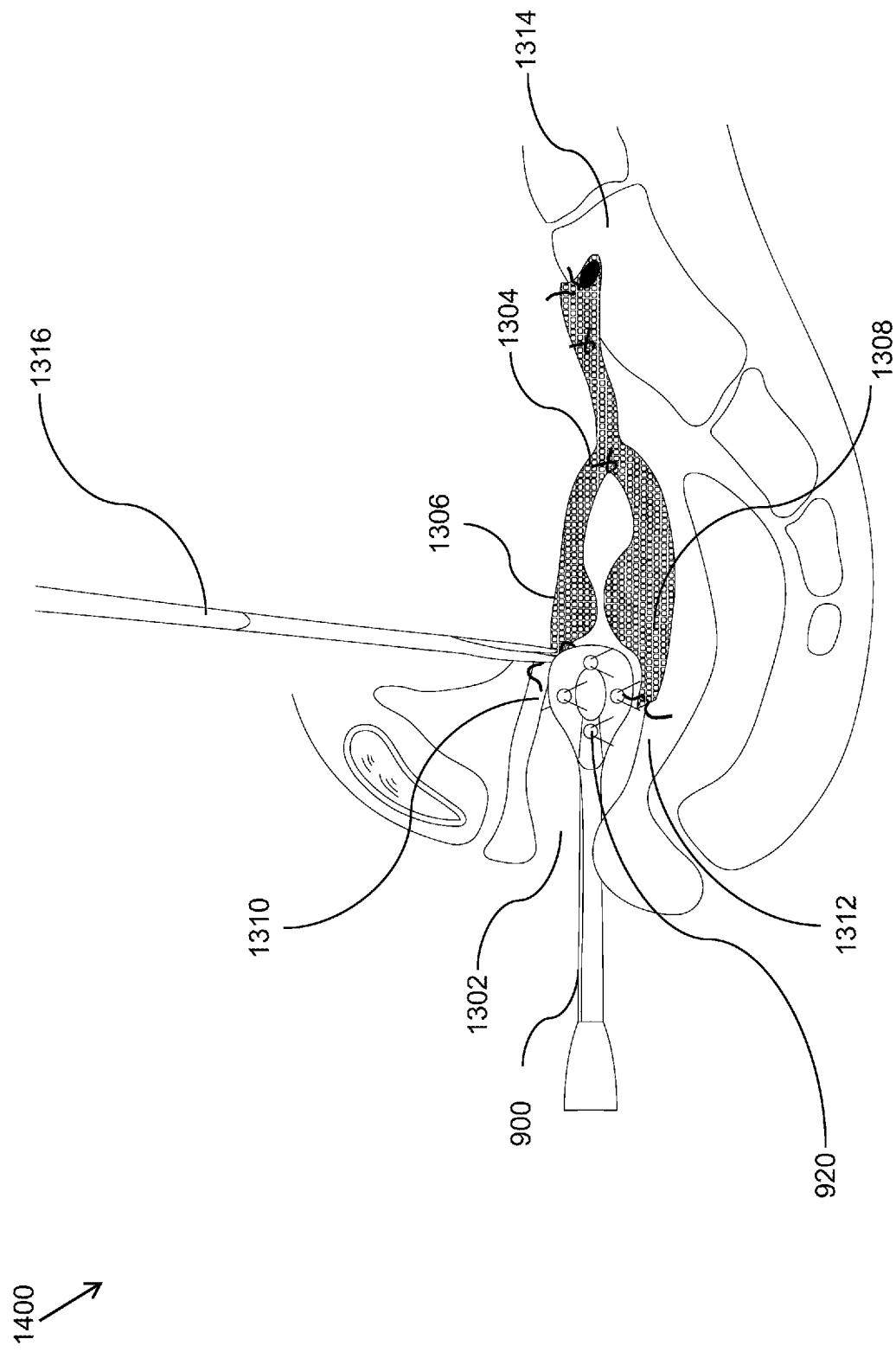
FIG. 14 illustrates placement of a medical device inside a body opening for manipulation, in accordance with an embodiment of the present invention.

FIG. 14 illustrates placement 1400 of the medical device 900 inside the vagina 1302 for manipulation of the bodily tissues. As shown, the medical device 900 projects light through the bodily tissues from the light sources 920 (e.g., 920a, 920b, 920c, and 920d as shown in FIG. 9) to assist in visualization of the tissues during surgery.

FIG. 15 illustrates a method 1500 of suturing the bodily implant 1304 within a patient's body. In some embodiments, the bodily implant 1304 is a mesh-based device such as a sling configured to support pelvic organs for the treatment of disorders such as prolapse, incontinence, and the like. In some embodiments, the bodily implant 1304 includes the first elongate member 1306 having the first end portion and the second end portion, and the second elongate member 1308 having the first end portion and the second end portion, as illustrated in FIGS. 13 and 14.

In accordance with other embodiments, other types of conventionally available implants can also be used in accordance with the present invention. For example, a single piece implant having only one elongate member can be used.

Referring now to FIG. 15 in conjunction with FIGS. 13 and 14, a method of suturing the bodily implant 1304 using a medical device such as the medical device 200 is described.

The method 1500 includes delivering of the bodily implant 1304 within the patient's body at step 1502. The bodily implant 1304 can be delivered in accordance with various surgical procedures such as through abdominal, transvaginal, and the like. Further, the delivery of the bodily implant 1304 can be performed through laparoscopic or laprotomic approaches. In accordance with various other embodiments, any conventional approach for delivery of the implant 1304 can be employed.

The method 1500 further includes advancing the medical device 200 into a body opening such as the vagina 1302 or an anal canal of the patient at step 1504. The medical device 200 includes the elongated portion 202 having the first width 216. The medical device 202 further includes the head portion 204 extending from the elongated portion 202. The head portion 204 has the second width 218 such that the second width 218 is more than the first width 216. The head portion 204 further includes the first flat surface 212 and the second flat surface 214. In some embodiments, the first flat surface 212 and the second flat surface 214 have greater width than the first width 216. In some embodiments, the first flat surface 212 and the second flat surface 214 have width equal to the width of the head portion (second width 218). The medical device 200 is inserted into the body opening through the vagina 1302. In embodiments described herein and hereafter, the medical device 200 is used to describe the methods and procedural steps. However, the medical device 100, 700, 800, 1000 or 1200 can also be employed in the similar manner.

In accordance with some embodiments, the method 1500 further includes attaching the first end portion of the first elongate member 1306 to the anterior vaginal wall 1310 and attaching the first end portion of the second elongate member 1308 to the posterior vaginal wall 1312 at step 1506. Further, the second end portion of the first elongate member 1306 and the second end portion of the second elongate member 1308 are attached to the sacrum 1314 of the patient at step 1508. During attachment of the first elongate member 1306 and the second elongate member 1308, the operator or the surgeon can use the medical device 200 for manipulating the bodily tissues and the elongate members 1306 and 1308.

The method 1500 further includes fixing a suture coupled to an end of the bodily implant 1304 with a bodily tissue at step 1510. The fixing of suture with the bodily tissue is done using one of the first flat surface 212 and the second flat surface 214 of the medical device 200. In embodiments, the medical device 200 having the first flat surface 212 and the second flat surface 214 is also used to manipulate the bodily tissue such as a vaginal tissue. The first flat surface 212 and the second flat surface 214 also act as a backstop during suturing by providing a substantially large surface area because of flat surfaces 212 and 214 that come in contact with a suture. The first flat surface 212 and the second flat surface 214 can also be used to spread the bodily tissue to facilitate suturing at a correct location. The operator or the surgeon can use either of the two flat surfaces 212 and 214 during suturing.

In some embodiments, the bodily implant 1304 includes a first suture at its first end and a second suture at its second end such that fixing the suture includes fixing the first suture to a first bodily tissue and fixing the second suture to a second bodily tissue by using one of the first flat surface 212 and the second flat surface 214 of the medical device 200. The first flat surface 212 and the second flat surface 214 assist in manipulating the bodily tissues such as the vaginal tissues. The manipulation of the bodily tissues includes pushing a vagina upward to assist suturing of the bodily implant. The manipulation of the bodily tissues may include expanding and/or stretching of the bodily tissues inside the vagina. The first flat surface 212 and the second flat surface 214 stretch and separate the bodily tissues inside the vagina (that facilitate stitching) and provide a flat surface/area for better suturing.

The method 1500 can further include adjusting tensions of the first elongate member 1306 and the second elongate member 1308 at step 1512. In some embodiments, the tension in the first elongate member 1306 can be different from the tension in the second elongate member 1308. In other embodiments, the tension of the first elongate member 1306 and the second elongate member 1308 can be kept same.

In some embodiments, the medical device 200 can also include a light source such as the light source 820 configured to project light 822 through the bodily tissues. The light source 820 is provided on the head portion 204 of the medical device 200. The method of suturing can also include projecting the light 822 from the light source 820 through the bodily tissues. The light source 820 has been described in conjunction with FIGS. 8A-9B.

In some embodiments, the head portion 204 of the medical device 200 can include an expandable member such as the expandable member 1214 configured to expand when inserted in a body opening such as a vagina 1302. The expandable member 1214 has been described in conjunction with FIG. 1200. In some embodiments, the method can also include expanding the expandable member 1214 once the expandable member 1214 is disposed inside the body opening. In some embodiments, the expandable member 1214 can include a set of flaps such as two flaps for example. The flaps are configured to contact one another in a collapsed configuration and detach from one another in an expanded configuration. In such cases, the movement of the flaps or pieces may cause expansion or collapse of the expandable member 1214. In some other embodiments, the expandable member 1214 can include an inflatable member or membrane (not shown) such that the inflatable member/membrane controls expansion or collapse of the expandable member 1214. Various other types of other conventional techniques can be used to cause the expandable member inflate or expand, thereby causing stretching of the bodily tissues.

In some more embodiments, the medical device 200 can also include an articulating member such as the articulating member 1020 coupled to the elongated portion 202 of the medical device 200 such that the elongated portion 202 is configured to move about the articulating member 1020. The articulating member 1020 has been described in conjunction with FIGS. 10A-11B. In accordance with these embodiments, the method 1500 can also include moving the elongated portion 202 with respect to the articulating member 1020 for manipulating the bodily tissue. The movement of the elongated member 202 with respect to the articulating member 1020 provides an ability to alter the angle of the proximal end portion 206 or handle 210 of the elongated portion 202. This improves the range of motion for the bodily tissue during surgery and/or inspection.

In some embodiments, a medical device includes an elongated portion and a head portion. The elongated portion has a proximal end portion and a distal end portion. The elongated portion has a first width. The head portion extends from the distal end portion of the elongated portion. The head portion includes a first flat surface on a first side and a second flat surface on a second side opposite the first side. The head portion has a second width. The second width is greater than the first width.

In some embodiments, the medical device is a tissue manipulator configured to manipulate the bodily tissue. In some embodiments, the manipulator is a vaginal manipulator configured to manipulate vaginal tissues. In some embodiments, the first flat surface and the second flat surface have width equal to the second width of the head portion.

In some embodiments, the device includes an expandable member configured to expand once the medical device is disposed inside the body opening. In some embodiments, the device includes an articulating member coupled to the elongated portion such that the elongated portion is configured to move about the articulating member.

In some embodiments, a medical device for manipulating a bodily tissue, the medical device includes an elongated portion, a head portion, and a light source. The elongated portion has a proximal end portion and a distal end portion. The elongated portion has a first width. The head portion extends from the distal end portion of the elongated portion. The head portion has a second width. The second width is greater than the first width. The light source is provided on the head portion. The light source is configured to project light through the bodily tissue.

In some embodiments, the light source is configured to emit light different than a white light.

In some embodiments, a method of suturing a bodily implant includes delivering a bodily implant within a patient's body; advancing a medical device into a body opening, the medical device including an elongated portion having a first width; and a head portion extending from the elongated portion, wherein the head portion includes a first flat surface and a second flat surface, the head portion having a second width such that the second width is more than the first width; and fixing a suture coupled to an end of the bodily implant with a bodily tissue by using one of the first flat surface and the second flat surface of the medical device.

In some embodiments, the bodily implant is a mesh-based device.

In some embodiments, the method includes inserting the bodily implant inside the patient's body through an abdominal access.

In some embodiments, the bodily implant includes a first elongate member and a second elongate member, the method further comprising attaching a first end portion of the first elongate member to an anterior vaginal wall; attaching a first end portion of the second elongate member to a posterior vaginal wall; and attaching a second end portion of the first elongate member and a second end portion of the second elongate member to a sacrum.

In some embodiments, the method includes adjusting tensions of the first elongate member and the second elongate member.

In some embodiments, the method includes inserting the medical device through a vaginal opening.

In some embodiments, the method includes projecting light through the bodily tissue from a light source, wherein the light source is provided on the head portion.

In some embodiments, the head portion includes an expandable member, the method further comprising expanding the expandable member once the expandable member is disposed inside the body opening.

In some embodiments, the elongated portion includes an articulating member, the method further comprising moving the elongated portion with respect to the articulating member for manipulating the bodily tissue.

In some embodiments, the manipulating the bodily tissue comprises pushing a vagina upward to assist suturing of the bodily implant.

In some embodiments, the end of the bodily implant is a first end of the bodily implant, the bodily tissue is a first bodily tissue, the method further comprising fixing the suture coupled to a second end of the bodily implant with a second bodily tissue by using one of the first flat surface and the second flat surface of the medical device.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical device comprising:
an elongated portion having a proximal end portion and a distal end portion, the elongated portion having a first width, the elongated portion having a longitudinal axis;
a head portion extending from the distal end portion of the elongated portion, wherein the head portion includes a first surface on a first side and a second surface on a second side opposite the first side, the head portion having a second width, the second width being greater than the first width, the head portion defining a perimeter portion around a circumference of the head portion;
an expandable member coupled to the head portion, the expandable member configured to expand from a first configuration to a second configuration, the expandable member configured to increase the surface area of the first surface and the second surface of the head portion when expanded to the second configuration;
a handle;
an articulating member coupled to the handle and the proximal end portion of the elongated portion, the distal end portion of the elongated portion being configured to move about the articulating member such that the articulating member alters an angle defined by the longitudinal axis of the elongated portion and the longitudinal axis of the handle; and
a plurality of light sources provided on both the first and second surfaces and disposed around the perimeter portion, wherein each of the plurality of light sources is configured to project light through the bodily tissue such that both the first and second surfaces can be used for suturing.

2. The medical device of claim 1, wherein the expandable member defines a hole in a center of the head portion.

3. The medical device of claim 1, wherein the head portion includes a first rounded portion that bulges out of the first surface and a second rounded portion that bulges out of the second surface.

4. The medical device of claim 1, wherein the first and second surfaces of the head portion are configured to extend to edges of the expandable member.

5. The medical device of claim 1, wherein the expandable member has a third width when in the first configuration and a fourth width when in the second configuration, the fourth width being larger than the third width, the fourth width being larger than the first and second widths, the expandable member configured to expand from the first configuration to the second configuration when the medical device is disposed inside a body opening thereby increasing the surface area of the first surface and the second surface of the head portion.

6. The medical device of claim 1, wherein the handle has a larger diameter than the elongated portion.

7. The medical device of claim 1, wherein the head portion includes a tapered section that tapers towards the elongated portion.

8. The medical device of claim 1, wherein the first and second surface are flat surfaces, and lateral sides of the flat surfaces are curved.

9. A medical device for manipulating a bodily tissue, the medical device comprising:
   an elongated portion having a proximal end portion and a distal end portion, the elongated portion having a first width;
   a head portion extending from the distal end portion of the elongated portion, the head portion having a second width, the second width being greater than the first width, the head portion defining a top flat surface and a bottom flat surface opposite to the top flat surface, the head portion defining a perimeter portion around a circumference of the head portion; and
   a plurality of light sources provided on both the top and bottom flat surfaces and disposed around the perimeter portion, wherein each of the plurality of light sources is configured to project light through the bodily tissue such that both the top and bottom flat surfaces can be used for suturing.

10. A method of suturing a bodily implant, the method comprising:
   delivering a bodily implant within a patient's body;
   advancing a medical device into a body opening, the medical device comprising:
      an elongated portion having a first width;
      a head portion extending from the elongated portion, wherein the head portion includes a top surface and a bottom surface, the bottom surface being opposite to the top surface, the head portion having a second width such that the second width is more than the first width, the head portion defining a through-hole extending between and through the top surface and the bottom surface, the through-hole defining a hollow center in a middle portion of the head portion, the head portion defining a perimeter portion that fully surrounds the hollow center; and
      a plurality of light sources disposed around the perimeter portion of the head portion of the elongated portion, the plurality of light sources include light sources disposed on the top surface of the head portion and light sources disposed on the bottom surface of the head portion such that both the top and bottom flat surfaces can be used for suturing;
   projecting light through the bodily tissue from the plurality of light sources; and
   fixing a suture coupled to an end of the bodily implant with a bodily tissue by using one of the top surface and the bottom surface of the head portion.

11. The method of claim 10, wherein the bodily implant is a mesh-based device.

12. The method of claim 10 further comprising:
   inserting the bodily implant inside the patient's body through an abdominal access.

13. The method of claim 10, wherein the bodily implant includes a first elongate member and a second elongate member, the method further comprising:
   attaching a first end portion of the first elongate member to an anterior vaginal wall;
   attaching a first end portion of the second elongate member to a posterior vaginal wall; and
   attaching a second end portion of the first elongate member and a second end portion of the second elongate member to a sacrum.

14. The method of claim 13 further comprising:
   adjusting tensions of the first elongate member and the second elongate member.

15. The method of claim 10 further comprising:
   inserting the medical device through a vaginal opening.

16. The method of claim 10, wherein the medical device further includes a handle, and an articulating member coupled to the handle and a proximal end portion of the elongated portion, the method further comprising:
   moving the elongated portion in relation to the handle via the articulating member for manipulating the bodily tissue.

17. The method of claim 16, wherein the manipulating the bodily tissue comprises pushing a vagina upward to assist suturing of the bodily implant.

18. The method of claim 10, wherein the end of the bodily implant is a first end of the bodily implant, the bodily tissue is a first bodily tissue, the method further comprising:
   fixing the suture coupled to a second end of the bodily implant with a second bodily tissue by using one of the top surface and the bottom surface of the medical device.

* * * * *